(12) United States Patent
Hupp et al.

(10) Patent No.: US 9,623,404 B2
(45) Date of Patent: Apr. 18, 2017

(54) METAL ORGANIC FRAMEWORKS FOR THE CATALYTIC DETOXIFICATION OF CHEMICAL WARFARE NERVE AGENTS

(71) Applicant: NORTHWESTERN UNIVERSITY, Evanston, IL (US)

(72) Inventors: Joseph T. Hupp, Northfield, IL (US); Omar K. Farha, Morton Grove, IL (US); Michael J. Katz, Evanston, IL (US); Joseph E. Mondloch, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/585,718

(22) Filed: Dec. 30, 2014

(65) Prior Publication Data

US 2016/0175827 A1    Jun. 23, 2016

Related U.S. Application Data

(60) Provisional application No. 61/922,370, filed on Dec. 31, 2013.

(51) Int. Cl.
*B01D 53/04* (2006.01)
*B01J 31/16* (2006.01)
(Continued)

(52) U.S. Cl.
CPC .......... *B01J 31/1691* (2013.01); *A62B 7/10* (2013.01); *A62D 3/35* (2013.01); *A62D 9/00* (2013.01); *B01D 53/04* (2013.01); *B01J 20/226* (2013.01); *B01J 35/023* (2013.01); *B01J 35/1019* (2013.01); *B01J 35/1023* (2013.01); *B01J 35/1028* (2013.01); *B01J 35/1057* (2013.01); *B01J 35/1061* (2013.01); *C07F 7/006* (2013.01); *A62D 2101/02* (2013.01); *B01D 2253/204* (2013.01); *B01D 2253/306* (2013.01); *B01D 2253/308* (2013.01);
(Continued)

(58) Field of Classification Search
CPC .............. B01D 53/04; B01D 2253/204; B01D 2253/306; B01D 2253/308; B01D 2257/408; B01D 2259/4583; B01J 20/226
USPC ........ 95/90; 96/108; 423/210, 236; 502/150, 502/152, 153, 401; 55/DIG. 33, DIG. 35
See application file for complete search history.

(56) References Cited

U.S. PATENT DOCUMENTS 8,883,676 B1 * 11/2014 Peterson ................ B01J 20/226 502/401
9,216,404 B1 * 12/2015 Peterson ................ B01J 20/226
(Continued)

OTHER PUBLICATIONS

Mondloch et al. "Vapor-Phase Metalation by Atomic Layer Deposition in a Metal-Organic Framework" Jul. 2013, Journal of the American Chemical Society, pp. 10294-10297.*
(Continued)

*Primary Examiner* — Frank Lawrence
(74) *Attorney, Agent, or Firm* — The Marbury Law Group PLLC

(57) ABSTRACT

A method of using a metal organic framework (MOF) comprising a metal ion and an at least bidendate organic ligand to catalytically detoxify chemical warfare nerve agents including exposing the metal-organic-framework (MOF) to the chemical warfare nerve agent and catalytically decomposing the nerve agent with the MOF.

32 Claims, 7 Drawing Sheets

(NU-1000)

(51) Int. Cl.
| | |
|---|---|
| *B01J 35/10* | (2006.01) |
| *B01J 35/02* | (2006.01) |
| *C07F 7/00* | (2006.01) |
| *A62D 3/35* | (2007.01) |
| *A62B 7/10* | (2006.01) |
| *B01J 20/22* | (2006.01) |
| *A62D 9/00* | (2006.01) |
| *A62D 101/02* | (2007.01) |

(52) U.S. Cl.
CPC ............... *B01D 2257/408* (2013.01); *B01D 2259/4583* (2013.01); *B01J 2531/46* (2013.01); *B01J 2531/48* (2013.01); *B01J 2531/49* (2013.01)

(56) References Cited

U.S. PATENT DOCUMENTS

| | | | |
|---|---|---|---|
| 2010/0081186 A1* | 4/2010 | Lee | A62D 3/36 435/177 |
| 2011/0010826 A1* | 1/2011 | Kaskel | A62D 5/00 2/457 |
| 2011/0126713 A1* | 6/2011 | Legare | A62B 23/02 96/135 |

OTHER PUBLICATIONS

Ferey, G., "Hybrid Porous Solids: Past, Present," Future. Chemical Society Reviews, vol. 37, pp. 191-214 (2008).
Farha, O.K., et al., "De Novo Synthesis of a Metal-Organic Framework Material Featuring Ultrahigh Surface Area and Gas Storage Capacities," Nature Chemistry, vol. 2, pp. 944-948 (2010).
Wilmer, C.E., et al., "Structure-Property Relationships of Porous Materials for Carbon Dioxide Separation and Capture," Energy & Environmental Science, vol. 5, pp. 9849-9856, (2012).
Raushel, F. M., "Catalytic Detoxification," Nature, vol. 469, pp. 310-311 (2011).
Peterson, G.W., et al., "Removal of Chlorine Gases From Streams of Air Using Reactive Zirconium Hydroxide Based Filtration Media," Ind. Eng. Chem. Res., vol. 51, pp. 2675-2681, (2012).
Wagner, G.W., et al., "Effect of Adsorbed Water and Surface Hydroxyls on the Hydrolysis of VX, GD, and HD on Titania Materials: The Development of Self-Decontaminating Paints," Ind. Eng. Chem. Res., vol. 51, pp. 3598-3603, (2012).
Bandosz, T. J. et al., "Reactions of VX, GD, and HD with Zr(OH)4: Near Instantaneous Decontamination of VX," J. Phys. Chem., vol. 116, pp. 11606-11614, (2002).
Wang, S., et al., "Organophophorous Ester Degradation by Chromium(III) Terephthalate Metal—Organic Framework (MIL-101) Chelated to N,N-Dimethylaminopyridine and Related Aminopyridines," ACS Appl. Mater. Interfaces, 2013. (5): p. 1269-1278.
Smith, B. M., "Catalytic methods for the destruction of chemical warfare agents under ambient conditions," Chem. Soc. Rev., 2008. (37): p. 470-478.
Bigley, et al., "Catalytic Mechanism for Phosphotriesterases," Biochim. Biophys. Acta, 2013. 1834(1): p. 443-453.
Katz, M. J. et al., "Simple and Compelling Biomimetic Metal-Organic Framework Catalyst for the Degradation of Nerve Agent Simulants," Angew Chem Int Ed. 2013. (53): p. 497-501.
Peterson, G.W. et al., "Detoxification of Chemical Warfare Agents by CuBTC," J. Porous Mater, 2013. (21): p. 121-126.
Peterson, G. W. et al., "Effects of pelletization pressure on the physical and chemical properties of the metal—organic frameworks Cu3(BTC)2 and UiO-66," Microporous and Mesoporous Materials, vol. 179, pp. 48-53, (2013).
Li, H., et al., "Design and Synthesis of an Exceptionally Stable and Highly Porous Metal-Organic Framework," Nature, 1999. 402(6759): p. 276-279.
Wilmer, C.E., et al., "Large-Scale Screening of Hypothetical Metal-Organic Frameworks," Nature Chemistry, 2012. 4(2): p. 83-89.
Furukawa, H., et al., Ultrahigh Porosity in Metal-Organic Frameworks, Science, 2010. 329(5990): p. 424-428.
Chae, H.K., et al., "A Route to High Surface Area, Porosity and Inclusion of Large Molecules in Crystals," Nature, 2004. 427(6974): p. 523-527.

* cited by examiner

UiO-66

- $Ti_xZr_yHf_z(\mu_3\text{-}OH)_4(\mu_3\text{-}O)_4(O_2)_{12}$ (where $x + y + z = 6$)
- 12 linkers coordinate $Zr_6$
- Four proximal $\mu_3$-OH groups per $Zr_6$

NU-1000

- $Zr_xHf_yTi_z(\mu_3\text{-}O)_4(\mu_3\text{-}OH)_4(H_2O)_4(OH)_4(O_2)_8$ (where $x + y + z = 6$)
- 8 linkers coordinate $Zr_6$
- Four proximal $\mu_3$-OH groups, four terminal water molecules and four terminal hydroxyl groups per $Zr_6$

METAL ORGANIC FRAMEWORKS FOR THE CATALYTIC DETOXIFICATION OF CHEMICAL WARFARE NERVE AGENTS

RELATED APPLICATIONS

This application claims the benefit of U.S. Provisional Application No. 61/922,370, filed Dec. 31, 2013, hereby incorporated by reference in its entirety.

STATEMENT REGARDING FEDERALLY SPONSORED RESEARCH OR DEVELOPMENT

This invention was made with government support under HDTRA1-10-1-0023 awarded by the Defense Threat Reduction Agency and DE-AC05-06OR23100 (SubK No. 10-20903 DOE Oak Ridge Tenn.) awarded by the Department of Energy. The government has certain rights in the invention.

FIELD

The present invention is directed to metal-organic frameworks as catalysts and sorbents for the capture and detoxification of chemical warfare nerve agents.

BACKGROUND

Extensive research over the past few years has focused on the synthesis and characterization of highly tunable, microporous materials with high internal surface areas. Metal-Organic Frameworks (MOFs) are a crystalline subset of these materials that have shown promise for a wide array of gas, vapor, and liquid applications ranging from storage, separation, and catalysis. MOFs are comprised of at least ditopic organic linkers and metal ions that self-assemble into 3-dimensional porous structures. Example MOFs are illustrated in FIGS. 1a-d. MOF development has accelerated in the past decade because of favorable performance characteristics as a result of their internal high surface area, porosity, stability, and tunability.

SUMMARY OF THE INVENTION

Embodiments of the invention are drawn to (a) the development of MOF structures for catalytic detoxification of chemical warfare nerve agents, and (b) integration of these structures into air respiratory systems to filter and destroy toxic nerve agents. High performing MOFs enable a significant increase in the rate of chemical detoxification and a significant increase in the overall safety for personnel exposed to chemical warfare nerve agents.

An embodiment relates to a metal-organic framework (MOF) comprising the coordination product of a metal ion and at least bidentate organic ligand, wherein the metal ion and the organic ligand are selected to assemble a MOF configured to of catalytically detoxify chemical warfare nerve agents.

A further embodiment relates to a method of using a detoxification system that is filled with MOF or the MOF is part of a stacked bed where the toxic nerve agents flow through a detoxification system.

Another embodiment relates to a method of using a MOF to detoxify gas streams containing highly toxic chemical warfare nerve agents, such as in a filter or canister incorporated into a gas respirator or gas mask, by exposing the metal-organic-framework (MOF) to the chemical warfare nerve agent and catalytically decomposing the nerve agent with the MOF.

A further embodiment includes a method of manufacturing a MOF-based gas respirator for filtering and detoxifying nerve agents.

Additionally, another embodiment relates to a method of making MOFs for catalytically detoxifying chemical warfare nerve agents with a half-life rate of no greater than 45 minutes.

DETAILED DESCRIPTION

Figure 1A:
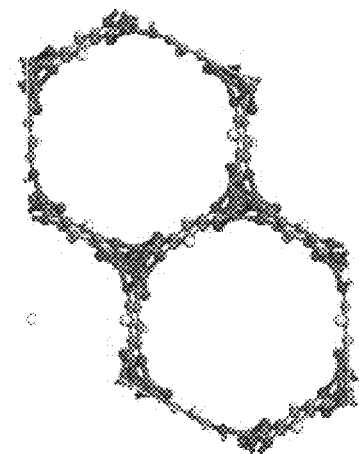
FIGS. 1a-1d are ball and stick illustrations of metal-organic frameworks including (a) CoMOF74, (b) NU100, (c) AlMIL53, and (d) NU125.
Figure 1B:
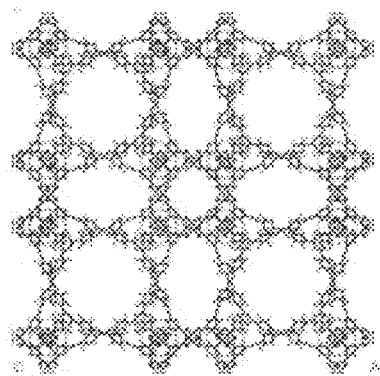
Figure 1C:
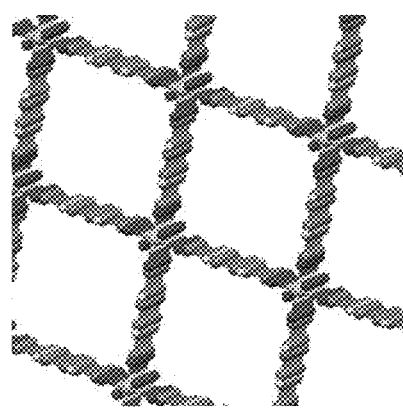
Figure 1D:
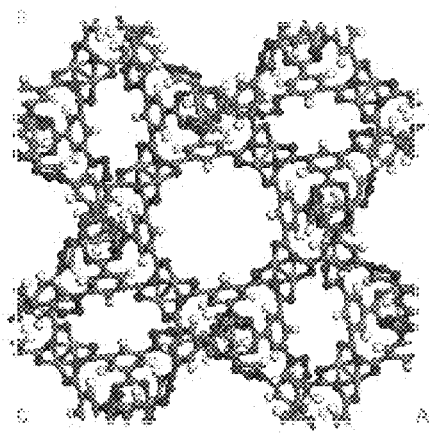

Multiple global military events have increased the need to find rapid, safe, and effective strategies to catalytically detoxify banned chemical warfare agents. Many of these agents contain moieties that can be degraded through hydrolysis. Degradable moieties include organophosphorus bonds and phosphate ester bonds that are found in nerve agents such as Sarin or VX. Table 1 includes a non-exhaustive list of nerve agents that may be detoxified by embodiment discussed in more detail below. These nerve agents are among the most toxic chemicals known to mankind. Solutions are needed to improve the safety of bulk destruction of banned chemical weapon stockpiles, to improve personnel safety from airborne agents, and to improve the containment of nerve agent spills and/or leaks. Some heterogeneous materials, such as modified activated carbon or metal oxides, display a few of the desired characteristics for detoxification of nerve agents. However, these materials also suffer from many undesirable characteristics such as low sorptive capacities, low effective active site loading, limited catalytic lifetime, slow catalytic rates, and material degradation. Embodiments herein overcome the limitations and challenges associated with the prior art sorbent-based heterogeneous nerve agent detoxification.

TABLE 1

Nerve Agents

| | | | |
|---|---|---|---|
| Hydrogen cyanide | Ethyldichloro- arsine (ED) | Methyldichloro- arsine (MD) | Phenyldichloro- arsine (PD) |
| Sulfur Mustard (HD, H, HT, HL, HQ) | Nitrogen mustard (NH1, NH2, NH3) | Tabun (GA) | Sarin (GB) |
| Cyclosarin (GF) | GV | EA-3148 | Methyl fluorophosphoryl homocholine iodid (MFPhCh) |
| VG | VM | VP | VR |
| Novichok agents | Phosphine oxime (CX) | Chlorine | Chloropicrin (PS) |
| Diphosgene (DP) | Disulfur decafluoride | Agent 15 (BZ) | Dimethylheptyl- pyran (DMHP) |
| Kolokol-1 | LSD-25 | PAVA spray | Pepper spray (OC) |
| Mace ® (CN) | CR | | |

As used herein, detoxification is the process of chemically converting highly toxic chemical warfare nerve agents into corresponding by-products that have much lower toxicity, such as little or no toxicity.

Embodiments of the MOFs disclosed herein include MOFs in which the metal cluster of the MOF ranges between and includes twelve-coordinate and three-coordinate. The embodiments of the MOFs disclosed herein may have pore size diameters ranging from 4 to 55 Å. Embodiments of the MOFs disclosed herein have a BET measured surface area between 500 to 5000 m$^2$/g. Depending on the method of synthesis, as discussed in more detail below, the MOF particles may have sizes ranging from 100 nm to 5 mm. Embodiments of the methods herein may be used to detoxify nerve agents provided in a gas phase, vapor phase, liquid phase, or an aerosol. In embodiments, the nerve agents are exposed to the MOFs in a pressure range of 0.33 and 1.48 standard atmospheres, a temperatures between −40° C. and 50° C., and a pH between 0 and 14.

The naturally occurring phosphotriesterase (PTE) enzyme, found in *pseudomonas diminuta, flavobacterium, agrobacterium radiobacter*, and *chryseobacterium balustinum* bacterium, is known to be highly active in the hydrolysis of phosphate ester bonds and organophosphorus bonds, the types of bonds found in many chemical warfare nerve agents. The active site of the phosphotriesterase enzyme contains a hydroxyl group bridged by two Zn(II) atoms (Zn—OH—Zn). This arrangement works cooperatively to cleave the P—O bond(s) and thus detoxifying the agent. While the Zn—OH—Zn moiety illustrates one type of the catalytic active sites used to detoxify nerve agents, other mechanisms and other active sites exist. MOFs are materials with tunable properties which may scaffold a high density of active sites useful for detoxification, such as metal to metal bridging hydroxyl or oxo groups.

Figure 3A:
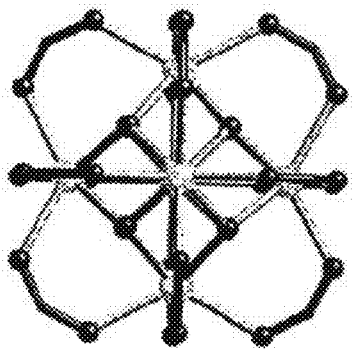
FIG. 3a-3b are ball and stick illustrations of the metal node/cluster of (a) UiO-66 illustrating hydroxyl groups bridged between two zirconium atoms in a twelve-connected $Zr_6$ cluster, and (b) NU-1000 illustrating the bridging hydroxyl groups, terminal hydroxyl groups, and terminal water molecules in an eight-connected $Zr_6$ cluster (metal node).
Figure 3B:
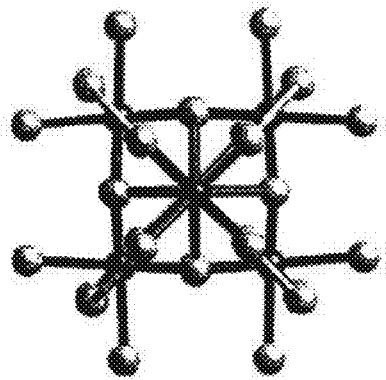

Given their outstanding thermal, mechanical, and hydrolytic stability, MOFs containing nodes/clusters with individual metals or any combination of metals from group 4 on the periodic table (e.g. Ti, Zr, or Hf) may be used for catalytic detoxification of nerve agents. These MOFs have nodes or clusters with general molecular formulas of $Ti_xZr_yHf_z(\mu_3\text{-OH})_4(\mu_3\text{-O})_4(O_2)_{12}$ (where x+y+z=6) in the hydrated form (e.g. UiO-66 MOF shown in FIG. 3a having 12 linkers coordinate $Zr_6$ with four proximal $\mu_3$-OH groups per $Zr_6$) and $Ti_xZr_yHf_z(\mu_3\text{-O})_6(O_2)_{12}$ (where x+y+z=6) in the dehydrated form or $Zr_xHf_yTi_z(\mu_3\text{-O})_4(\mu_3\text{-OH})_4(H_2O)_4(OH)_4(O_2)_8$ (where x+y+z=6) (NU-1000 shown in FIG. 3b having 8 linkers coordinate $Zr_6$ with four proximal $\mu_3$-OH groups, four terminal water molecules and four terminal hydroxyl groups per $Zr_6$). The individual values of x, y, and z can be any integer from 0 to 6 as long as their sum equals to 6. The affix "μ" is used to signify that a group so designated bridges two or more centers of coordination and its subscript denotes the number of centers of coordination.

Figure 2A:
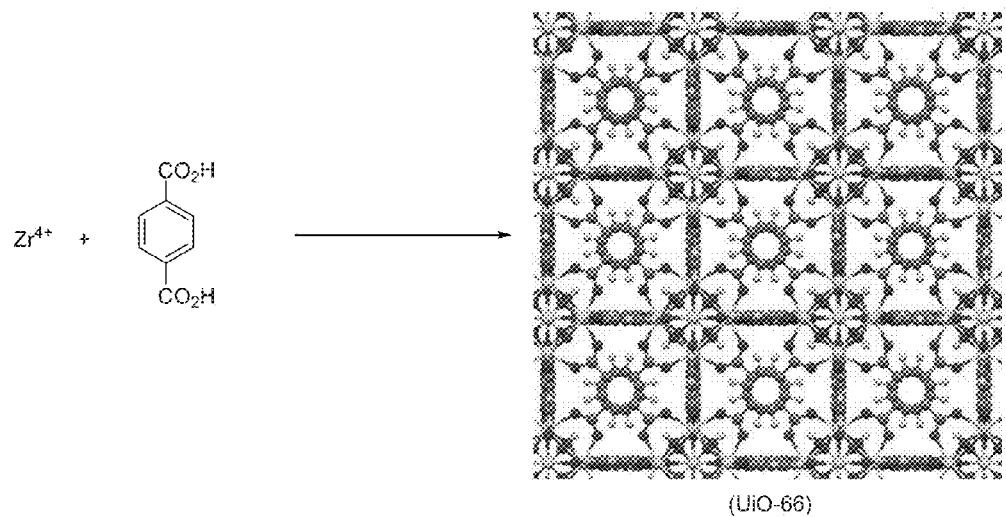
FIGS. 2a-2b are synthesis schemes to produce metal-organic frameworks (shown as ball and stick illustrations) including (a) UiO-66 and (b) NU-1000.

These MOFs may have a terminal hydroxyl group or a terminal water molecule connected to a metal cluster selected from the group consisting of titanium, zirconium, hafnium, and combinations thereof. Additionally, these MOFs contain several Zr—OH—Zr type moieties (i.e. the oxygen atom of the bridging hydroxyl group is connected to two metal atoms, such as two Ti, Zr or Hf atoms, or combinations thereof), similar to the bridging Zn—OH—Zn active site found in naturally occurring enzymes discussed above. For example as illustrated in FIG. 2a, UiO-66 is made from heating a mixture of $Zr^{4+}$ ions and terephthalic acid in dimethylformamide which results in a MOF with surface areas ranging from 800 to 1600 m$^2$/g with pore size diameters of ~8 Å. These MOFs can selectively adsorb nerve agents. Thus, the MOFs act as a catalyst to detoxify the chemical warfare nerve agents and act as a sorbent that selectively adsorbs the chemical warfare nerve agents.

Figure 4A:
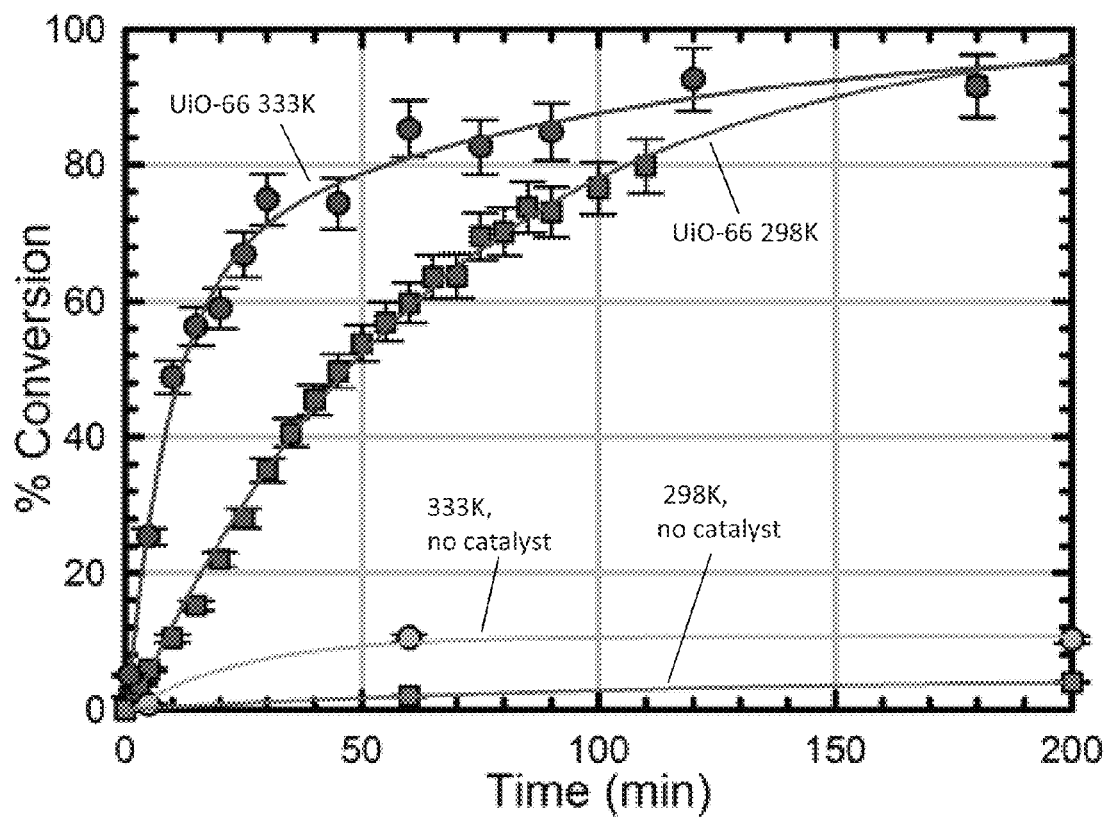
FIG. 4a are conversion profiles (percentage detoxified versus time in minutes) of the detoxification of a chemical warfare nerve agent simulant, methyl paraoxon, using UiO-66. This plot shows a detoxification half-life of 45 minutes at 298K.

Considering the incredibly high toxicity of nerve agents, experiments were conducted using less toxic simulants, including methyl paraoxon (dimethyl 4-nitrophenyl phosphate) and p-nitrophenyl diphenyl phosphate. The rate of degradation was observed using UV-vis spectroscopy by following the formation of UV/blue-adsorbing byproducts. In an example, the hydrolysis was carried out in the presence of 6 mol % UiO-66 in an aqueous solution containing 0.45 M N-ethylmorpholine (as a buffer at pH=10). FIG. 4a illustrates detoxification profiles for the UiO-66 catalyzed hydrolysis of methyl paraoxon at 298K (squares) and 333K (circles) as a function of time. The detoxification profiles show half-lives of 45 and 10 minutes, at 298 K and 333K, respectively. Additionally, as shown in FIG. 4a, the background detoxification reaction, i.e. hydrolysis in the absence of the MOF catalyst, is significantly slower and shows the detoxification plateauing at ~5% and ~12% at 298K (squares) and 333K (circles) respectively.

To validate the heterogeneous nature of the catalysis, the UiO-66 MOF was removed by filtration and the reaction was further monitored. As expected, no catalysis was further observed. Additionally, the surface area of the UiO-66 material was measured and found to decrease from 1450 m$^2$/g (UiO-66 prior to detoxification catalysis measurements) to 750 m$^2$/g (UiO-66 after detoxification catalysis measurements). This loss in surface area after catalysis is not due to a loss in crystallinity or structure integrity as the PXRD pattern for the as-synthesized UiO-66 matched the PXRD pattern for the UiO-66 after catalysis. However, the loss in surface area after catalysis is attributed to the porous nature of the MOF, i.e. the pores of the MOF captured and adsorbed the nerve agent simulant and/or byproducts. From these measurements, the MOF was determined to have a nerve agent simulant and/or byproduct capacity of 0.3-0.7 $g_{(nerve\ agent)}/g_{(MOF)}$, such as 0.4-0.6 $g_{(nerve\ agent)}/g_{(MOF)}$, such as ~0.47 $g_{(nerve\ agent)}/g_{(MOF)}$.

Considering the small pore apertures of UiO-66 (~6 Å) and the relatively larger size of methyl paraoxon (~11 Å×4.5 Å), much of the catalysis occurs on the exterior surface of the MOF particle. Dynamic-light scattering (DLS) measurements and scanning electron microscope (SEM) images indicate UiO-66 MOF particle sizes of 400 nm. However, the ratio between the interior surface and the exterior surface decreases as the particle size decreases. Therefore, for UiO-66, particle size plays a role in the rate of detoxification. Depending on the synthesis procedures, UiO-66 particles can be synthesized as small as 100 nm.

Figure 2B:
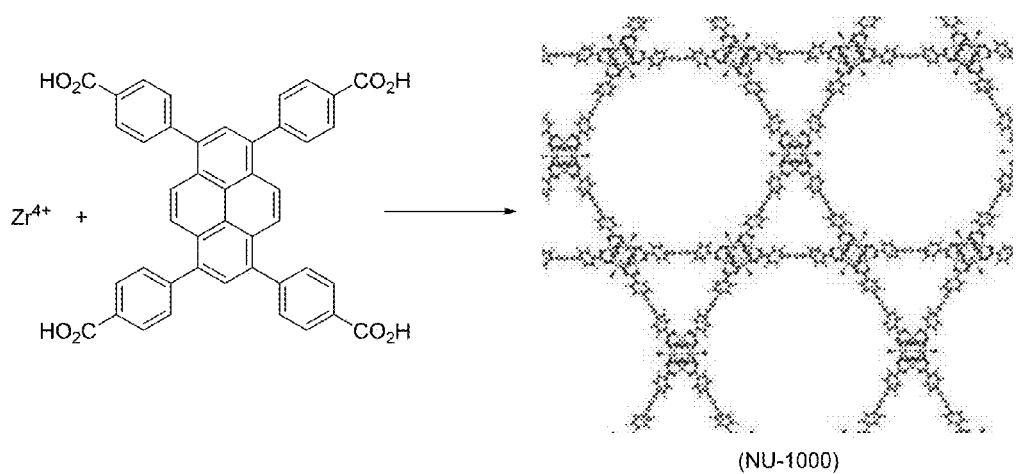

To promote interior catalysis and overcome the challenge of exclusive surface or near surface catalysis, a similar highly stable zirconium MOF was synthesized, NU-1000, illustrated in FIG. 2b. NU-1000 may be made from heating a mixture of $Zr^{4+}$ ions and 1,3,6,8-tetrakis(p-benzoic-acid) pyrene in dimethylformamide resulting in a MOF with a surface area of 2320 $m^2/g$. Depending on which individual or combination of metal precursors from group 4 on the periodic table is used, NU-1000 forms metal nodes or clusters with a molecular formula of $Zr_xHf_yTi_z(\mu_3\text{-}O)_4(\mu_3\text{-}OH)_4(H_2O)_4(OH)_4(O_2)_8$, where x+y+z=6 (FIG. 3b) in the hydrated form and $Zr_xHf_yTi_z(\mu_3\text{-}O)_8(O_2)_8$ where x+y+z=6 in the dehydrated form. The individual values of x, y, and z can be any integer from 0 to 6 as long as their sum equals to 6. Additionally, NU-1000 produces a honeycomb like structure with one exceptionally wide 31 Å channel and a smaller 10 Å wide channel. The large channel is large enough to adsorb sizeable nerve agent molecules to allow interior catalysis as well as promote rapid diffusion and mass transfer.

Figure 4B:
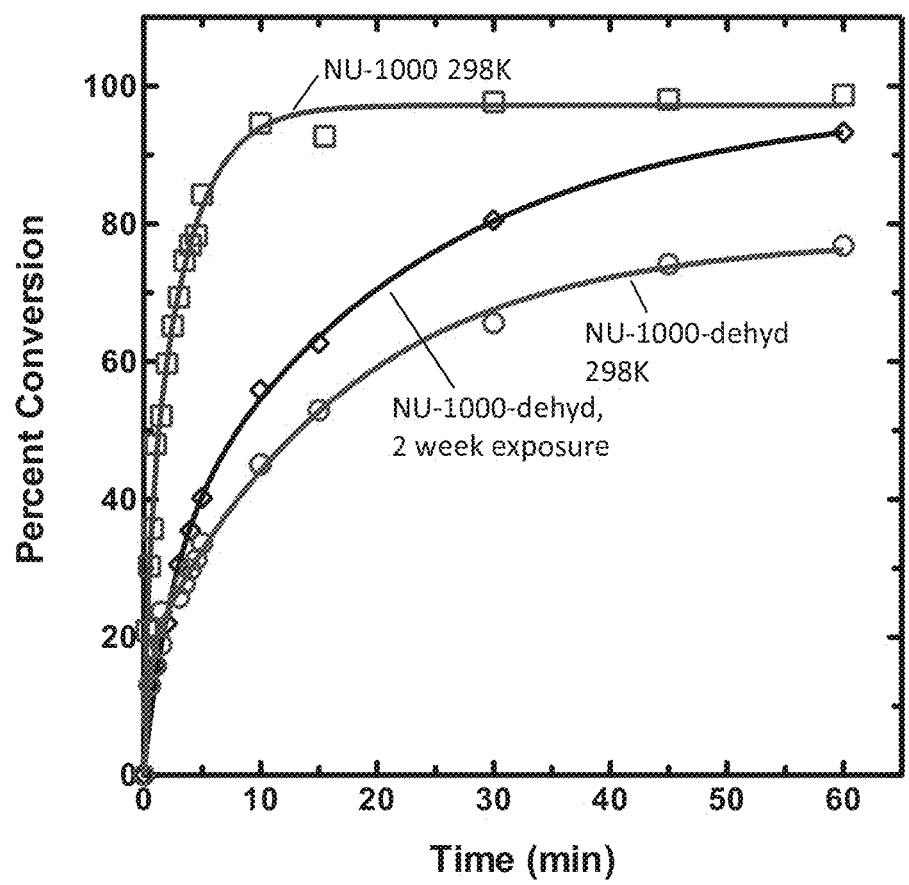
FIG. 4b are conversion profiles (percentage detoxified versus time in minutes) of the detoxification of a chemical warfare nerve agent simulant, methyl paraoxon, using NU-1000 and dehydrated NU-1000. This plot shows a detoxification half-life of 1.5 minutes at 298K.

NU-1000 was used to catalyze the hydrolysis of nerve agent simulates under the same conditions as UiO-66 discussed above, i.e. 6 mol % NU-1000 in an aqueous solution containing 0.45 M N-ethylmorpholine (as a buffer at pH 10). FIG. 4b illustrates detoxification profiles for the hydrolysis of methyl paraoxon at room temperature (298K) with NU-1000 (squares), dehydrated NU1000 (circles), and dehydrated NU-1000 exposed to an ambient atmosphere for 2 weeks (diamonds). As anticipated, a faster half-life for the detoxification of methyl paraoxon in the presence of NU-1000 was measured. The half-lives for detoxification of methyl paraoxon with of NU-1000 and dehydrated NU-1000 15 minutes and 1.5 minutes, respectively. Even more compelling, NU-1000 was further used to catalyze the hydrolysis of the highly toxic known nerve agent GD. Remarkably, NU-1000 yields a detoxification reaction half-life of just 36 min, representing a nearly 80-fold increase in activity over the best MOF to date. Of note, the molar activity of NU-1000 is much higher than metal oxides. Thus, while hundreds of milligrams of metal oxide are typically required, a mere 30 milligrams of NU-1000 was used the detoxify the same quantity of GD.

In addition to highly active bridging hydroxyl groups, bridging oxo groups also exhibit very high rates of catalysis. This was illustrated after NU-1000 was thermally dehydrated at 300° C. to remove terminal aquo and hydroxyl ligands, thus converting bridging hydroxyl groups in NU-1000 to bridging oxo groups in dehydrated NU-1000. The bridging oxo groups may be connected to two atoms selected from the group consisting of titanium, zirconium, hafnium and combinations thereof.

Oxo bridges are also found in a variety of other MOF structures. As with the thermal treatment of other metal-oxides or other MOFs, coordinatively unsaturated metal sites are exposed after the removal of hydrating ligands. These coordinatively unsaturated metal sites act as potent Lewis acids because of their ability to bind to electron rich moieties, such as those found in chemical warfare nerve agents. This binding enhances the hydrolytic detoxification of nerve agents. A half-life of merely 1.5 minutes was observed for the catalytic degradation of methyl paraoxon using dehydrated NU-1000 as the catalyst under the same reaction conditions as the aforementioned UiO-66 and NU-1000 catalysis.

The above embodiments illustrate the highly effective ability of MOFs to catalytically detoxify chemical warfare nerve agents. This detoxification can be accomplished on a bulk scale to safely and rapidly detoxify banned chemical stockpiles or to mitigate and detoxify nerve agent spills and leaks. Additionally, given the highly porous nature of MOFs, this detoxification can be accomplished on a personnel scale through the use MOF-based air respirators. MOF-based air respirators can capture toxic nerve agents through their highly sorptive abilities while also catalytically detoxifying nerve agents. This is a significant improvement over other sorbent-based heterogeneous detoxification materials.

Figure 5A:
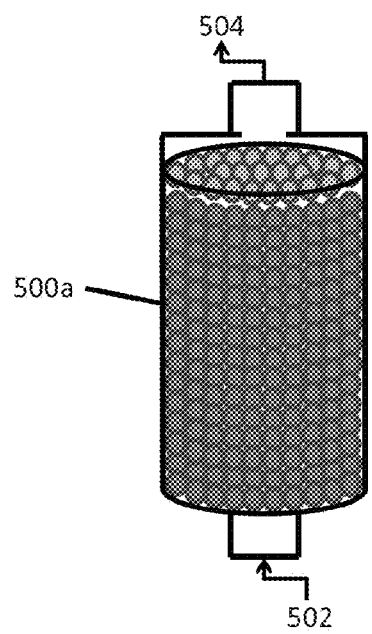
FIG. 5a-c are representative illustrations of MOF-based detoxification systems including (a) a MOF pellet-filled container, (b) a MOF disk-filled container, and (c) a monolithic MOF-filled container.
Figure 5B:
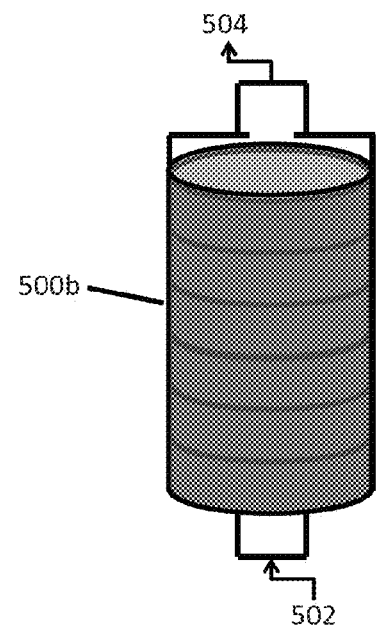
Figure 5C:
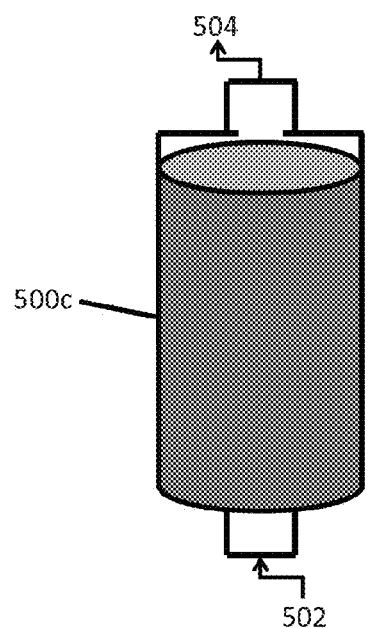

Additional embodiments include MOF-based detoxification systems that include containers comprising the MOFs discussed above. As illustrated in FIG. 5a-5c, these systems include (a) a MOF pellet-filled container 500a, (b) a MOF disk-filled container 500b, and (c) a monolithic MOF-filled container 500c. In an embodiment, the container includes a MOF that is part of a stacked bed comprising layers of non-MOF materials. Any suitable non-MOF materials may be used, such as one or more of metal oxide, metal hydroxide, activated carbon, or aluminosilicate material. The containers 500a, 500b, 500c include one or more gas inlets 502 through which toxic gas is provided to the MOF within and one or more gas outlets 504 though which detoxified gas exits the containers 500a, 500b, 500c.

Figure 6A:
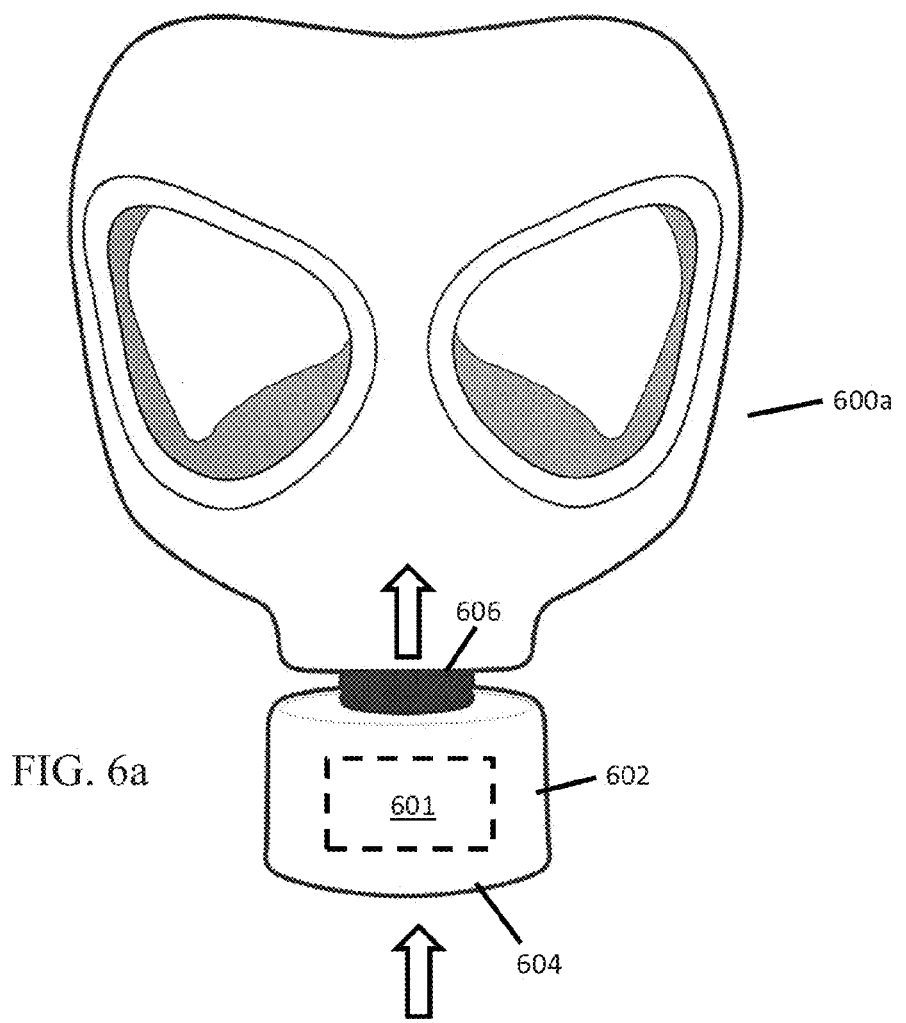
FIGS. 6a and 6b are schematic illustrations of MOF-based detoxification systems including (a) a gas mask and (b) a filtration device.
Figure 6B:
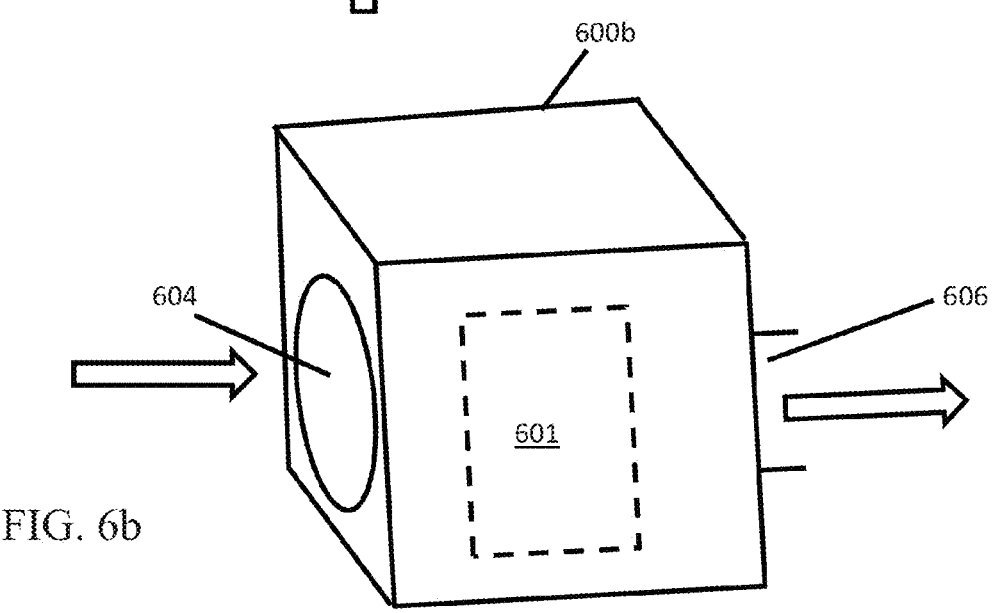

FIGS. 6a and 6b illustrate additional embodiments of MOF-based chemical warfare reagent detoxification device. The detoxification device 600a illustrated in FIG. 6a is a gas mask with a respirator cartridge 602. The gas respirator cartridge 602 includes a gas inlet 604 and a gas outlet 606 and a container 601 (e.g., filter or canister) containing the MOF. The container may be directly filled with MOF material (pellet, disk or monolithic body) or the cartridge may be provided with a MOF filled container 500a, 500b, or 500c as described in the previous embodiment.

The alternative embodiment detoxification device 600b illustrated in FIG. 6b is an area detoxification device that can detoxify an area (e.g., a structure, such as a building or a vehicle). The detoxification system 600b includes a gas inlet 604, a gas outlet 606 and MOF material container 601. Device 600b may be a portable unit that may include an internal fan (not shown) which may be placed in building or other structure that has suffered a gas attack to remove the gas from the structure. Alternatively, the device 600b may be an air inlet filter installed in a structure (e.g., building, underground shelter, etc.) or vehicle which the MOF acts as a catalyst to detoxify the chemical warfare nerve agents and acts as a sorbent that selectively adsorbs the chemical warfare nerve agents present in the air to reduce or prevent the chemical warfare nerve agents from reaching inside the structure or vehicle.

An embodiment of the method includes exposing the chemical warfare nerve agent to a metal-organic-framework (MOF), and catalytically decomposing the nerve agent with the MOF. The chemical warfare nerve agent may be an organophosphate, an organophosphorus compound, or combinations thereof. For example, the chemical warfare nerve agent may comprises cyanogen chloride, hydrogen cyanide, ethyldichloroarsine (ED), methyldichloroarsine (MD), phenyldichloroarsine (PD), lewisite (L), sulfur mustard (HD, H, HT, HL, HQ), nitrogen mustard (NH1, NH2, NH3), Tabun (GA), Sarin (GB), Soman (GD), Cyclosarin (GF), GV, Methyl fluorophosphoryl homocholine iodid (MFPhCh), EA-3148, VE, VG, VM, VP, VR, VX, Novichok agents, phoshene oxime (CX), chlorine, chloropicrin (PS), phosgene (CG), diphosgene (DP), disulfur decafluoride, agent 15 (BZ), dimethylheptylpyran (DMHP), EA-3167, kolokol-1, LSD-25, PAVA spray, sleeping gas, pepper spray (OC), CS, mace® (CN), CR, and combinations thereof. In an embodiment, the container is a respirator cartridge. An embodiment of the method includes filling the cartridge with a MOF (e.g. pellets, disks or a monolithic MOF body) capable of detoxifying chemical warfare nerve agents. In an embodiment, the MOF is part of a stacked bed containing other layers of materials in a respirator cartridge.

An embodiment includes a method of making a MOF comprising reacting a metal ion and an at least bidentate organic ligand, wherein the metal ion and the organic ligand are selected assemble a MOF to catalytically detoxify chemical warfare nerve agents. In an embodiment, the MOF catalytically detoxifies the nerve agent at a rate with a half-life no greater than 45 minutes second measured at 298 K, catalysis loading of 6 mol %, chemical warfare nerve agent concentration of 0.025 mol/L, and buffered solution of pH 10.

The following references disclose aspects of the fabrication of MOFs and are hereby incorporated by reference in their entireties:

1. Li, H., et al., Design and synthesis of an exceptionally stable and highly porous metal-organic framework. Nature, 1999. 402(6759): p. 276-279.
2. Ferey, G., Hybrid porous solids: past, present, future. Chemical Society Reviews, 2008. 37(1): p. 191-214.
3. Wilmer, C. E., et al., Large-scale screening of hypothetical metal-organic frameworks. Nature Chemistry, 2012. 4(2): p. 83-89.
4. Farha, O. K., et al., De novo synthesis of a metal-organic framework material featuring ultrahigh surface area and gas storage capacities. Nature Chemistry, 2010. 2(11): p. 944-948.
5. Furukawa, H., et al., Ultrahigh Porosity in Metal-Organic Frameworks. Science, 2010. 329(5990): p. 424-428.
6. Ferey, G., et al., A chromium terephthalate-based solid with unusually large pore volumes and surface area. Science, 2005. 309(5743): p. 2040-2042.
7. Chae, H. K., et al., A route to high surface area, porosity and inclusion of large molecules in crystals. Nature, 2004. 427(6974): p. 523-527.
8. Wilmer, C. E., et al., Structure-property relationships of porous materials for carbon dioxide separation and capture. Energy & Environmental Science, 2012. 5(12): p. 9849-9856.
9. Raushel, F. M. Catalytic detoxification. Nature 2011 (469): p. 310-311.
10. Peterson, G. W. & Rossin, J. A. Removal of chlorine gases from streams of air using reactive zirconium hydroxide based filtration media. Ind Eng Chem Res, 2012. (51): p. 2675-2681.
11. Wagner, G. W., Peterson, G. W. & Mahle, J. J. Effect of adsorbed water and surface hydroxyls on the hydrolysis of VX, GD, and HD on titania materials: the development of self-decontaminating paints. Ind Eng Chem Res, 2012. (51): p. 3598-3603.
12. Bandosz, T. J. et al. Reactions of VX, GD, and HD with Zr(OH) 4: Near Instantaneous Decontamination of VX. J Phys Chem C, 2012. (116): p. 11606-11614.
13. Wang, S., Bromberg, L., Schreuder-Gibson, H. & Hatton, T. A. Organophophorous Ester Degradation by Chromium(III) Terephthalate Metal-Organic Framework (MIL-101) Chelated to N,N-Dimethylaminopyridine and Related Aminopyridines. ACS Appl. Mater. Interfaces, 2013. (5): p. 1269-1278.
14. Smith, B. M. Catalytic methods for the destruction of chemical warfare agents under ambient conditions. Chem. Soc. Rev., 2008. (37): p. 470-478.
15. A. N. Bigley, F. M. Raushel, Catalytic Mechanism for Phosphotriesterases. Biochim. Biophys. Acta, 2013. 1834(1): p. 443-453.
16. Katz, M. J. et al. Simple and Compelling Biomimetic Metal-Organic Framework Catalyst for the Degradation of Nerve Agent Simulants. Angew Chem Int Ed. 2013. (53): p. 497-501.
17. Peterson, G. W. & Wagner, G. W. Detoxification of chemical warfare agents by CuBTC. J Porous Mater, 2013. (21): p. 121-126.

Although the foregoing refers to particular preferred embodiments, it will be understood that the invention is not so limited. It will occur to those of ordinary skill in the art that various modifications may be made to the disclosed embodiments and that such modifications are intended to be within the scope of the invention. All of the publications, patent applications and patents cited herein are incorporated herein by reference in their entirety.

What is claimed is:

1. A metal-organic framework (MOF) comprising the coordination product of a metal ion and an at least bidentate organic ligand, wherein the metal ion and the organic ligand are selected to assemble a MOF configured to catalytically detoxify chemical warfare nerve agents, wherein a metal node of MOF comprises a molecular formula of $Ti_xZr_yHf_z(\mu_3-O)_6(O_2)_{12}$, where $x+y+z=6$ and where the oxygen atoms from the organic ligand are included in the formula.

2. The metal-organic framework of claim 1, wherein the rate of catalytic detoxification comprises a measured catalytic half-life of no greater than 45 min measured at pH 10 with chemical warfare nerve agent concentration of 0.025 mol/L, containing 6 mol % of catalyst, and at 298 K.

3. The metal-organic framework of claim 1, wherein the MOF acts as a catalyst to detoxify the chemical warfare nerve agents and acts as a sorbent that selectively adsorbs the chemical warfare nerve agents.

4. The metal-organic framework of claim 1, wherein the MOF contains at least one bridging hydroxyl group.

5. The metal-organic framework of claim 4, wherein an oxygen atom of the at least one bridging hydroxyl group is connected to two atoms selected from the group consisting of titanium, zirconium, hafnium and combinations thereof.

6. The metal-organic framework of claim 1, wherein the MOF contains at least one terminal hydroxyl group or at least one terminal water molecule on a metal node.

7. The metal-organic framework of claim 6, wherein the terminal hydroxyl group or the terminal water molecule is connected to a metal cluster selected from the group consisting of titanium, zirconium, hafnium, and combinations thereof.

8. The metal-organic framework of claim 1, wherein the MOF contains bridging oxo groups.

9. The metal-organic framework of claim 8, wherein the bridging oxo group is connected to two atoms selected from the group consisting of titanium, zirconium, hafnium and combinations thereof.

10. The metal-organic framework of claim 1, wherein the MOF is a product of dehydration and contains unsaturated metal sites.

11. The metal-organic framework of claim 10, wherein the metal ion is selected from the group consisting of titanium, zirconium, hafnium, and combinations thereof.

12. The metal-organic framework of claim 1, where in the metal cluster of the MOF ranges between and includes twelve-coordinate and three-coordinate.

13. The metal-organic framework of claim 1, wherein the organic ligand is made with the precursor terephthalic acid.

14. The metal-organic framework of claim 1, wherein the MOF has pore size diameters ranging from 4 to 55 Å.

15. The metal-organic framework of claim 1, wherein the MOF has a BET measured surface area between 500 to 5000 m$^2$/g.

16. The metal-organic framework of claim 1, wherein the MOF is formed into a particle that has a size ranging from 100 nm to 5 mm.

17. A chemical warfare reagent detoxification device comprising a metal-organic framework (MOF) comprising the coordination product of a metal ion and an at least bidentate organic ligand, wherein the metal ion and the organic ligand are selected to assemble a MOF configured to catalytically detoxify chemical warfare nerve agents, wherein a metal node of the MOF comprises a molecular formula of $Ti_xZr_yHf_z(\mu_3\text{-}O)_4(\mu_3\text{-}OH)_4(H_2O)_4(OH)_4(O_2)_8$ or $Ti_xZr_yHf_z(\mu_3\text{-}O)_8(O_2)_8$, where x+y+z=6 and where the oxygen atoms from the organic ligand are included in the formula, wherein the MOF comprises pellets, disks, or a monolith and the device comprises a respirator cartridge.

18. The device of claim 17, wherein the MOF comprises NU-1000.

19. The device of claim 17, wherein the MOF is part of a stacked bed comprising layers of non-MOF materials.

20. A method of using a metal organic framework (MOF) comprising a metal ion and an at least bidendate organic ligand to catalytically detoxify chemical warfare nerve agents comprising:
exposing the MOF to the chemical warfare nerve agent; and
catalytically decomposing the nerve agent with the MOF, wherein a metal node of the MOF comprises $Ti_xZr_yHf_z(\mu_3\text{-}O)_4(\mu_3\text{-}OH)_4(H_2O)_4(OH)_4(O_2)_8$ or $Ti_xZr_yHf_z(\mu_3\text{-}O)_8(O_2)_8$, where x+y=6 and where the oxygen atoms from the organic ligand are included in the formula.

21. The method of claim 20, wherein the chemical warfare nerve agent is an organophosphate, an organophosphorus compound, or combinations thereof.

22. The method of claim 20, wherein the nerve agent comprises cyanogen chloride, hydrogen cyanide, ethyldichloroarsine (ED), methyldichloroarsine (MD), phenyldichloroarsine (PD), lewisite (L), sulfur mustard (HD, H, HT, HL, HQ), nitrogen mustard (NH1, NH2, NH3), Tabun (GA), Sarin (GB), Soman (GD), Cyclosarin (GF), GV, Methyl fluorophosphoryl homocholine iodid (MFPhCh), EA-3148, VE, VG, VM, VP, VR, VX, Novichok agents, phoshene oxime (CX), chlorine, chloropicrin (PS), phosgene (CG), diphosgene (DP), disulfur decafluoride, agent 15 (BZ), dimethylheptylpyran (DMHP), EA-3167, kolokol-1, LSD-25, PAVA spray, sleeping gas, pepper spray (OC), CS, CN, CR, and combinations thereof.

23. The method of claim 20, wherein the nerve agent comprises a gas phase, vapor phase, liquid phase, or an aerosol.

24. The method of claim 20, wherein exposing the MOF is performed in a pressure range of 0.33 and 1.48 standard atmospheres, a temperatures between −40° C. and 50° C., and a pH between 0 and 14 and the MOF comprises UiO-66 or NU-1000.

25. A method of making a respirator cartridge comprising filling a cartridge with a MOF capable of detoxifying chemical warfare nerve agents, wherein the metal ion and the organic ligand are selected to assemble a MOF configured to catalytically detoxify chemical warfare nerve agents, wherein a metal node of the MOF comprises the molecular formula of $Ti_xZr_yHf_z(\mu_3\text{-}O)_4(\mu_3\text{-}OH)_4(H_2O)_4(OH)_4(O_2)_8$ or $Ti_xZr_yHf_z(\mu_3\text{-}O)_8(O_2)_8$, where x+y+z=6 and where the oxygen atoms from the organic ligand are included in the formula.

26. The method of claim 25, wherein the MOF is part of a stacked bed containing non-MOF layers of materials in a respirator cartridge.

27. The device of claim 17, wherein the metal node of the MOF comprises $Ti_xZr_yHf_z(\mu_3\text{-}O)_4(\mu_3\text{-}OH)_4(H_2O)_4(OH)_4(O_2)_8$.

28. The device of claim 17, wherein the metal node of the MOF comprises $Ti_xZr_yHf_z(\mu_3\text{-}O)_8(O_2)_8$.

29. The method of claim 20, wherein the metal node of the MOF comprises $Ti_xZr_yHf_z(\mu_3\text{-}O)_4(\mu_3\text{-}OH)_4(H_2O)_4(OH)_4(O_2)_8$.

30. The method of claim 20, wherein the metal node of the MOF comprises $Ti_xZr_yHf_z(\mu_3\text{-}O)_8(O_2)_8$.

31. The method of claim 25, wherein the metal node of the MOF comprises $Ti_xZr_yHf_z(\mu_3\text{-}O)_4(\mu_3\text{-}OH)_4(H_2O)_4(OH)_4(O_2)_8$.

32. The method of claim 25, wherein the metal node of the MOF comprises $Ti_xZr_yHf_z(\mu_3\text{-}O)_8(O_2)_8$.

* * * * *